United States Patent [19]

Morton

[11] 4,431,630
[45] Feb. 14, 1984

[54] DENTIFRICE COMPOSITION

[75] Inventor: Anthony J. Morton, Ashton-under-Lyne, England

[73] Assignee: Colgate-Palmolive Company, New York, N.Y.

[21] Appl. No.: 373,208

[22] Filed: Apr. 29, 1982

[30] Foreign Application Priority Data

May 8, 1981 [GB] United Kingdom ............... 8114137

[51] Int. Cl.$^3$ .............................................. A61K 7/18
[52] U.S. Cl. ...................................... 424/52; 424/57
[58] Field of Search ................................. 424/49–58

[56] References Cited

U.S. PATENT DOCUMENTS

| | | | |
|---|---|---|---|
| 4,036,950 | 7/1977 | Baines et al. | 424/57 |
| 4,123,517 | 10/1978 | Baines et al. | 424/57 |
| 4,238,476 | 12/1980 | Harvey | 424/52 |
| 4,264,580 | 4/1981 | Barberio | 424/57 |
| 4,301,143 | 11/1981 | Barberio | 424/57 |
| 4,350,680 | 9/1982 | Harvey et al. | 424/52 |

Primary Examiner—Shep K. Rose
Attorney, Agent, or Firm—Robert L. Stone; Herbert S. Sylvester; Murray M. Grill

[57] ABSTRACT

A dentifrice composition containing a water-soluble monofluorophosphate and a calcium salt polishing agent, principally dicalcium phosphate, and a surface active agent containing an anionic phosphate mono- and di- ester mixture. An alkali metal fluoride may be present in minor amount to the monofluorophosphate. The phosphate ester mixture improves retention of soluble fluoride.

7 Claims, No Drawings

DENTIFRICE COMPOSITION

The invention relates to a dentifrice composition. More particularly it relates to a dentifrice composition containing a water-soluble monofluorophosphate, in which the polishing material is a calcium salt, principally dicalcium phosphate.

Dentifrice containing a water-soluble monofluorophosphate, such as sodium monofluorophosphate and dicalcium phosphate polishing agent are known to be effective in reducing caries formation. This was demonstrated in the clinical test described by Naylor and Emslie in the British Dental Journal of July 4, 1967 at pages 17-23. Such dentifrices have been further described in U.S. Pat. Nos. 3,308,029 and 3,634,584.

Even in these dentifrices retention of soluble fluorine is less than optimum. Soluble fluorine retention with dicalcium phosphate polishing agent can be improved by using a binary fluoride system of alkali metal monofluorophosphate and alkali metal fluoride in which the monofluorophosphate predominates. An object of the present invention is that substantial improvement in soluble fluorine retention is obtained. This is achieved by including a mixture of anionic phosphate mono- and di-esters in the dentifrice composition.

Mixtures of anionic phosphate mono- and di-esters as a dentifrice additive have been disclosed in British Pat. Nos. 1,475,251 and 1,475,252 as well as in German Patent Publication No. 29 18 132. British Pat. No. 1,475,251 is directed to an oral preparation containing the combination of a cationic antibacterial agent and the anionic phosphate ester mixture. The presence of a fluoride such as sodium monofluorophosphate is optional. Dicalcium phosphate is disclosed as a possible polishing agent. However, nonionic polishing agents such as alumina or silica are preferred in view of their compatibility with the cationic antibacterial agent. Thus, there is no disclosure of particularly using both dicalcium phosphate and a fluoride with the anionic phosphate ester mixture.

British Pat. No. 1,475,252 discloses a toothpaste compatible with an unlined aluminum container containing a polishing material containing a substantial amount of hydrated alumina and the anionic phosphate ester mixture. Fluorides such as sodium monofluorophosphate are optional. Dicalcium phosphate may comprise a portion of the polishing material together with the hydrated alumina.

German Patent Disclosure No. 29 18 132 relates to a dental cream containing a calcium carbonate polishing material and a sodium alkyl sulphate surface active agent in which the anionic phosphate ester mixture can be used to reduce grain formation. Dicalcium phosphate may comprise a small amount of the mainly calcium carbonate polishing material.

In accordance with certain of its aspects this invention relates to a dentifrice composition consisting essentially of a non-toxic amount of a water-soluble monofluorophosphate, about 20-99% by weight of a polishing material consisting essentially of a calcium salt, at least about 50% by weight of said calcium salt being dicalcium phosphate and about 0.5-5% by weight of a water-soluble surface active material consisting essentially of a non-cationic surface active agent, said surface active agent containing at least about 0.1% by weight of said dentifrice of a mixture of an anionic phosphate monoester of the formula

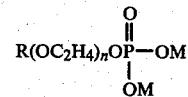

and anionic phosphate diester of the formula

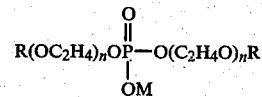

wherein R represents an alkyl group of 10-20 carbon atoms, n is an integer from 1 to 6 and M represents a hydrogen atom, an alkali metal cation or an ammonium group.

The alkali metal monofluorophosphate is preferably sodium monofluorophosphate. Sodium monofluorophosphate ($Na_2PO_3F$) is a water-soluble material which releases monofluorophosphate ions in water, and it may be mixed with the polishing material is any suitable amount. Such a dental composition is compatible with suitable amounts of other additives such as non-cationic surface-active agents, and gums as described herein. Sodium monofluorophosphate as commercially available may vary considerably in purity. It may be used in any suitable purity provided that any impurities do not substantially adversely affect the desired properties. In general, the purity is desirably at least about 80%. For best results, it should be at least 85%, and preferably at least 90% by weight of sodium monofluorophosphate with the balance being primarily impurities or by-products of manufacture such as sodium fluoride, or water-soluble sodium phosphate salts. Expressed in another way, the sodium monofluorophosphate employed should have a total fluoride content of above 12%, preferably above 12.7%; a content of not more than 1.5%, preferably not more than 1.2%, of free sodium fluoride; and a sodium monofluorophosphate content of at least 12%, preferably at least 12.1%, all calculated as fluorine.

The proportion of sodium monofluorophosphate in the dentifrice may be varied but should be an effective, non-toxic amount containing above 0.01% fluorine (100 p.p.m.). Suitable amounts are selected within the range of about 0.05% to a maximum of about 7.6% by weight. It is preferred that the sodium fluorophosphate salt be no more than 2%, and usually within the range of 0.05% to about 1%, by weight of the dentifrice.

It is within the scope of this invention that a minor proportion of alkali metal fluoride, such as sodium fluoride may be present together with the alkali metal monofluorophosphate, for instance in an amount to provide up to about 35% weight of the fluorine, typically about 30-35%.

In the present invention the surface active agent is non-cationic and contains the anionic phosphate mixture of mono- and di-esters set forth above.

The anionic phosphate esters used in the dentifrices of the invention are mixtures of mono- and di-esters of the formulas hereinabove set forth. Suitable materials are available from MoDo Kemi Aktiebolaget, formerly Berol Aktiebolaget, of Sweden under the name Berol (Berol is a Trade Mark) and may include an anionic tri-ester moiety too, as well as some non-ionic portion. Berol 729 has alkyl chain lengths of 16-18 carbon atoms and contains series of 4 ethylene oxide units. Berol 729 is generally used in neutralised or partially neutralised form.

Further anionic phosphate ester materials which may be used in acid or neutralised forms are Berol 525 which contains alkyl groups of 10-18 carbon atoms and series of 5 ethylene oxide units and Berol 513 which contains alkyl groups of 16-18 carbon atoms. Further, Berol 525 is also preferred in neutralised or partially neutralised form. Additional Berol anionic phosphate esters are available as Berol 521, Berol 724, and Berol 733. The weight ratio of mono-ester to di-ester may vary, but is typically from 1:10 to 10:1. The preferred grade of phosphate ester is Berol 513. Similar mixtures of anionic phosphate mono- and di-esters are also available from Albright and Wilson under the name Briphos.

When the acid forms of the anionic phosphate ester surface active agents are neutralised or partially neutralised, alkali metal cations, preferably sodium, or ammonium groups, are present.

The toothpastes may include an organic non-cationic surface active agent in addition to the anionic phosphate ester surface active agent. Such additional agent may be anionic, nonionic or amphoteric in nature, and it is preferred to employ as the surface-active agent a detersive material which imparts to the dentifrice detersive and foaming properties. Suitable types of such detergents are water-soluble salts of higher (i.e. having at least 12 carbon atoms) fatty acid monoglyceride monosulphates, such as the sodium salt of the monosulphated monoglyceride of hydrogenated coconut oil fatty acids, high alkyl sulphates, such as sodium lauryl sulphate, alkyl aryl sulphonates, such as sodium dodecyl benzene sulphonate, olefin sulphonates, such as sodium olefin sulphonate in which the olefin group contains 12-21 carbon atoms, higher alkyl sulphoacetates, higher fatty acid esters of 1,2-dihydroxy propane sulphonates, and the substantially saturated higher aliphatic acyl amides of lower (i.e. having not more than 4 carbon atoms) aliphatic amino carboxylic acid compounds, such as those having 12-16 carbons in the fatty acid, alkyl or acyl radicals. Examples of the last mentioned amides are N-lauroyl sarcosine, and the sodium, potassium and ethanolamine salts of N-lauroyl, N-myristoyl or N-palmitoyl sarcosine, which should be substantially free from soap or similar higher fatty acid material which tend to substantially reduce the effect of these compounds. The use of these sarcosine compounds in dentifrices is particularly advantageous since these materials exhibit a prolonged and marked effect in the inhibition of acid formation in the oral cavity due to breakdown of carbohydrates in addition to exerting some reduction in the solubility of tooth enamel in acid solutions.

Other particularly suitable surface-active materials include nonionic agents such as condensates of sorbitan monostearate with approximately 60 moles of ethylene oxide, condensates of ethylene oxide with propylene oxide condensates of propylene glycol ("Pluronics"— PLURONIC is a Trade Mark) and amphoteric agents such as quaternised imidazole derivatives, which are available under the trade name "Miranol" such as Miranol C2M. It is preferred that the total amount of surface active agent be about 0.5-5% by weight of the oral composition. At least about 0.1% of the dentifrice composition should be composed of the anionic phosphate ester surface active agent, preferably about 0.1-2% and most preferably about 0.25-1.5%.

The polishing material contains at least a major proportion of dicalcium phosphate, preferably dicalcium phosphate dihydrate. Other suitable dicalcium phosphate may be used, particularly dicalcium phosphate in anhydrous form. The dicalcium phosphate may be used singly as the sole polishing agent. It may also be used in combination with other polishing agents as the major ingredient (at least about 50% by weight) of the polishing material. The dicalcium phosphate may be considered as partially hydrated such as in a mixture of the dicalcium phosphate dihydrate and anhydrous dicalcium phosphate in any suitable ratio resulting from a blend or formed in situ in the manufacture of the dicalcium phosphate. A special feature of the present invention is that calcium carbonate such as natural chalk and preferably precipitated calcium carbonate may be used in minor proportion (i.e. up to about half by weight) of the polishing material. These polishing materials are employed in finely powdered form of any suitable particle size for effective polishing power.

In the case of the dicalcium phosphate and calcium carbonate mixtures, the ratio of these materials is variable and should be preferably from the range of about 99:1 to about 65:35 by weight, and usually about 25:1 to 3:1, depending upon the effects desired and the particular calcium phosphate and calcium carbonate used. In general, it is preferred to prepare dental creams having about 40-60% polishing material with dicalcium phosphate as the main polishing ingredient and from about 1 to 15% calcium carbonate (if present) in the dental cream. Other polishing materials may be added in suitable amount if desired such as calcium pyrophosphate, tricalcium phosphate or calcium polymetaphosphate. The total content of polishing agents will be usually at least about 20%, such as about 20-99% and particularly from about 20-75%, preferably about 40-60%, in toothpastes and at least about 70% in tooth powders.

In accordance with the present invention, the specified combinations of ingredients may be used in any suitable composition designed for application to the oral cavity which composition is referred to herein as a dentifrice composition. Such dentifrices may be in solid, liquid or paste form and include tooth pastes or dental creams, tooth powders, liquid dentifrices, and tablets. In the preparation of tooth powders, it is usually sufficient to admix mechanically the various solid ingredients.

In dental cream formulations, the liquids and solids should necessarily be proportioned to form a creamy mass of desired consistency which is extrudible from a collapsible aluminum or lead tube for example. In general, the liquids in the dental cream will comprise chiefly water, and materials such as glycerine, sorbitol, polyethylene glycol 400, or propylene glycol, including suitable mixtures thereof. It is advantageous usually to use a mixture of both water, and a humectant such as glycerine, sorbitol or mixtures thereof. Substantial improvement in accordance with this invention is affected when more than about 27% of water is present. The total liquid content will generally be about 20-75% by weight of the formulation; typically about 15-25% by weight of water and about 5-50% by weight of humectant. It is preferred to use also a gelling agent in dental creams such as the natural and synthetic gums and gum-like materials, e.g. Irish Moss, gum tragacanth, sodium carboxymethylcellulose, polyvinylpyrolidone, or starch. The Irish Moss and sodium carboxymethylcellulose are compatible particularly and are preferred gelling agents. The gum content is usually in an amount up to about 10% and preferably about 0.5–5% by weight of the formulation.

Other types of dentifrice compositions also will be formulated in known manner.

As mentioned above the polishing material consists essentially of a calcium compound as described. A small amount (e.g. up to about 2% by weight) of hydrated alumina may be incorporated into the dentifrice composition so as to eliminate or inhibit any tendency for separation or "bleeding" of the dental cream in the collapsible tube.

The dental creams may have any pH practicable for use e.g. about 4–10 preferably about 6–8. If necessary, acidifying agents or basic materials may be added to adjust the pH as desired. For example, a suitable acidifying agent such as phosphoric acid or citric acid or other weak acid may be employed in varying amount if necessary to adjust the pH of the dental cream.

Suitable flavouring or sweetening sialogogues may be employed in formulating a flavour of the compositions of the invention. Examples of suitable flavouring constituents include the flavouring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate and saccharine. Suitably, flavour and sweetening agent may together comprise from about 0.01 to 5% or more of the compositions of the present invention.

Various other materials also may be incorporated in the carrier. Examples thereof are colouring or whitening agents, preservatives, silicones, chlorophyll compounds, ammoniated materials such as urea, diammonium phosphate and mixtures thereof, and other constituents. These adjuvants are incorporated in the compositions of the present invention in amounts which do not substantially adversely affect the properties and characteristics suitably selected and used in proper amount depending upon the particular type of preparation involved.

The invention may be put into practice in various ways and a number of specific embodiments will be described to illustrate the invention with reference to the accompanying examples. All amounts are by weight unless otherwise indicated.

EXAMPLES 1A TO 4A AND 1B TO 4B

The dentifrice (dental cream) compositions set forth below are prepared by blending the gelling agent with the humectant and then adding a solution of the phosphate ester in water. Thereafter the polishing agent, surface active agent and monofluorophosphate are added followed by the flavouring agent. Early addition of the phosphate esters reduces phase separation and improves soluble fluorine retention. The creams are then deaerated and packaged in unlined aluminium tubes which are capped at the top and sealed by crimping at the bottom.

The dentifrice compositions are:

| COMPONENTS | Parts A | Parts B |
|---|---|---|
| Sorbitol (70% Aqueous Solution) | 16.00 | 16.00 |
| Glycerine | 6.00 | 6.00 |
| Sodium Carboxymethyl Cellulose | 1.00 | 1.00 |
| Sodium Saccharin | 0.18 | 0.18 |
| Sodium monofluorophosphate | 0.82 | 0.82 |
| Tetrasodium pyrophosphate | 0.50 | 0.50 |

-continued

| COMPONENTS | Parts A | Parts B |
|---|---|---|
| Nipastat preservative ($C_1$–$C_4$ alkyl-benzyl esters of p-hydroxybenzoic acid) | 0.25 | 0.25 |
| Dicalcium phosphate dihydrate | 48.00 | 48.00 |
| Sodium lauryl sulphate | 1.76 | 1.76 |
| Flavour | 0.80 | 0.80 |
| Colour (0.5% solution) | 0.20 | 0.20 |
| Berol 513 | — | 0.50 |
| Water (exclusive of water in sorbitol and colour solutions) | 24.49 | 23.99 |

Four different manufacturer grades of dicalcium phosphate (DCP) (as the dihydrate) indicated below as G-1, G-2, G-3, and G-4 were used in preparing the A and B dentifrices, Example 1A to 4A and 1B to 4B respectively. Tubes of each composition were aged for 3 months at room temperature and also for 3 months at 43° C. The soluble fluorine retention results are given in Table 1.

TABLE 1

| | | Soluble Fluorine Retention (PPM) | | | |
|---|---|---|---|---|---|
| | | Room Temperature | | 43° C. | |
| Example | D C P Grade | A | B | A | B |
| 1 | G-1 | 930 | 990 | 530 | 710 |
| 2 | G-2 | 970 | 1050 | 510 | 660 |
| 3 | G-3 | 850 | 920 | 280 | 420 |
| 4 | G-4 | 870 | 950 | 460 | 510 |

Marked improvement in retention of soluble fluorine, particularly under the accelerated aging conditions of 3 months at 43° C. were observed, with Dentifrice B samples (containing Berol 513) (Examples 1B to 4B) with all grades of DCP. The improvement is also noted when aging is carried out for 3 months at room temperature.

EXAMPLES 5B TO 8B; 9B TO 12B; 13B TO 16B; 17B TO 20B; AND 21B TO 24B

Improvements in soluble fluorine retention are also obtainable when Berol 513 in Dentifrice B is replaced by other anionic phosphate esters (Berol 521 (ex. 5B to 8B); 525 (ex. 9B to 12B); 724 (ex. 13B to 16B); 720 (ex. 17B to 20B); and 733 (ex. 21B to 24B).

EXAMPLES 26A TO 28A AND 25B TO 28B

The sorbitol in Dentifrices A and B of Examples 1 to 4 was replaced by glycerine, so that 22.00 parts of glycerine were present and the Nipastat preservative was replaced by its weight of water.

Upon aging for 3 months at room temperature and separately at 43° C., soluble fluorine retention levels with the several grades of DCP were generally similar with grades G-1 and G-2 (Examples 25A and B and 26A and B) and with grade G-3 at room temperature (Examples 27A and B). Marked improvement is observed at 43° C. with grades G-3 and G-4 (Examples 27A and B and 28A and B). The results observed are given in Table 2.

TABLE 2

| Example | D C P Grade | Soluble Fluorine Retention (PPM) | | | |
|---|---|---|---|---|---|
| | | Room Temperature | | 43° C. | |
| | | A | B | A | B |
| 25 | G-1 | 950 | 970 | 520 | 510 |
| 26 | G-2 | 970 | 970 | 510 | 510 |
| 27 | G-3 | 940 | 940 | 290 | 450 |
| 28 | G-4 | 910 | 930 | 440 | 570 |

EXAMPLES 29A TO 32A AND 29B TO 32B

The following Dentifrices were prepared in accordance with the procedure set forth in Examples 1 to 4, but with the addition of sodium fluoride.

| COMPONENTS | Parts A | Parts B |
|---|---|---|
| Glycerine | 22.000 | 22.000 |
| Sodium carboxymethyl cellulose | 0.900 | 0.900 |
| Sodium saccharin | 0.180 | 0.180 |
| Tetrasodium pyrophosphate | 0.250 | 0.250 |
| Sodium monofluorophosphate | 0.760 | 0.760 |
| Sodium fluoride | 0.100 | 0.100 |
| Dicalcium phosphate dihydrate | 48.00 | 48.00 |
| Sodium lauryl sulphate | 1.760 | 1.760 |
| Flavour | 0.800 | 0.800 |
| Dispersed dyes | 0.007 | 0.007 |
| Berol 513 | — | 0.500 |
| Water | 25.243 | 24.743 |

Upon aging separately for 6 and 12 months at room temperature substantial improvement in soluble fluorine retention levels was observed with the several grades of DCP. The results obtained are given in Table 3.

TABLE 3

| Example | D C P Grade | Soluble Fluorine Retention (PPM) Room Temperature | | | |
|---|---|---|---|---|---|
| | | 6 months | | 12 months | |
| | | A | B | A | B |
| 29 | G-1 | 960 | 1010 | 880 | 990 |
| 30 | G-2 | 1010 | 1080 | 900 | 1090 |
| 31 | G-3 | 950 | 1010 | 820 | 1090 |
| 32 | G-4 | 890 | 940 | 810 | 980 |

In the Examples, addition of the sodium monofluorophosphate or sodium monofluorophosphate and sodium fluoride to the dentifrices after addition of the polishing agents results in further improvement in soluble fluorine retention.

I claim:

1. A toothpaste dentifrice composition consisting essentially of a non-toxic amount of about 0.05-7.6% by weight of a water-soluble monofluorophosphate, an alkali metal fluoride present in amount to provide up to about 35% by weight of the fluorine, the remainder being provided by the said monofluorophosphate, about 20-75% by weight of a polishing material consisting essentially of a calcium salt member selected from the group consisting of dicalcium phosphate as the single calcium salt polishing material and calcium salt polishing material of at least half by weight of dicalcium phosphate with a member selected from the group consisting of calcium carbonate, calcium pyrophosphate, tricalcium phosphate and calcium polymetaphosphate and about 0.05-5% by weight of a water-soluble surface active material consisting essentially of a non-cationic surface active agent, said non-cationic surface active agent containing an anionic phosphate ester mixture in an amount of at least about 0.1% by weight of the said dentifrice, the said anionic phosphate ester mixture being a mixture of an anionic phosphate monoester of the formula:

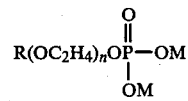

and anionic phosphate diester of the formula:

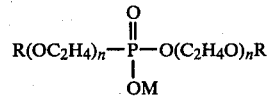

wherein R represents an alkyl group of 10-20 carbon atoms, n is an integer from 1 to 6 and M represents a member selected from the group consisting of hydrogen atom of an alkali metal cation or an ammonium group, wherein said anionic phosphate mixture improves the retention of soluble fluorine in said dentifrice.

2. The dentifrice composition as claimed in claim 1 wherein the said dicalcium phosphate is present in amount of about 40-60% by weight.

3. The dentifrice composition as claimed in claim 1 in which the said water-soluble monofluorophosphate is sodium monfluorophosphate.

4. The dentifrice composition as claimed in claim 1 in which the said alkali metal fluoride is present in amount to provide about 30-35% by weight of the fluorine.

5. The dentifrice composition as claimed in claim 3 in which the alkali metal fluoride is sodium fluoride.

6. The dentifrice composition as claimed in claim 1 in which the said dicalcium phosphate is the only polishing agent present in the said polishing material.

7. The dentifrice composition as claimed in claim 1 in which the alkyl groups in the anionic phosphate ester contain 16-18 carbon atoms.

* * * * *